United States Patent
Dzenitis et al.

(10) Patent No.: US 7,412,356 B1
(45) Date of Patent: Aug. 12, 2008

(54) DETECTION AND QUANTIFICATION SYSTEM FOR MONITORING INSTRUMENTS

(75) Inventors: John M. Dzenitis, Danville, CA (US); Claudia K. Hertzog, Houston, TX (US); Anthony J. Makarewicz, Livermore, CA (US); Bruce D. Henderer, Livermore, CA (US); Vincent J. Riot, Oakland, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 0 days.

(21) Appl. No.: 11/700,686

(22) Filed: Jan. 30, 2007

(51) Int. Cl.
  *G06F 19/00* (2006.01)
  *G06F 17/40* (2006.01)

(52) U.S. Cl. .............................. 702/189; 702/1; 702/19; 702/22; 702/85; 702/104; 702/127; 702/187; 702/190; 702/191; 702/193

(58) Field of Classification Search .............. 702/1, 702/19, 22, 23, 26, 27, 30, 31, 32, 85, 104, 702/127, 187, 189, 190, 191, 193, 194, 195
See application file for complete search history.

(56) References Cited

U.S. PATENT DOCUMENTS

| | | | | |
|---|---|---|---|---|
| 2,679,639 A * | 5/1954 | Locher | ....................... | 702/85 |
| 3,855,456 A * | 12/1974 | Summers et al. | ............ | 700/286 |
| 3,927,308 A * | 12/1975 | Summers et al. | ............ | 702/199 |
| 4,275,439 A * | 6/1981 | Kuwata | ....................... | 700/32 |
| 5,749,907 A * | 5/1998 | Mann | ............................ | 607/27 |
| 5,798,701 A * | 8/1998 | Bernal et al. | ................ | 340/628 |
| 5,875,420 A * | 2/1999 | Piety et al. | ................... | 702/182 |
| 6,073,089 A * | 6/2000 | Baker et al. | ................. | 702/185 |
| 6,245,517 B1 | 6/2001 | Chen et al. | | |
| 6,526,801 B2 * | 3/2003 | Kouznetsov et al. | ......... | 73/1.03 |
| 6,691,042 B2 | 2/2004 | Weng et al. | | |
| 7,096,125 B2 * | 8/2006 | Padmanabhan et al. | ....... | 702/24 |
| 7,102,514 B2 * | 9/2006 | Berry | ......................... | 340/540 |
| 2002/0121126 A1 * | 9/2002 | Kouznestov et al. | ......... | 73/1.03 |
| 2003/0065409 A1 * | 4/2003 | Raeth et al. | ................... | 700/31 |
| 2003/0148332 A1 | 8/2003 | Taylor et al. | | |
| 2003/0219797 A1 | 11/2003 | Zhao et al. | | |
| 2004/0088406 A1 * | 5/2004 | Corley et al. | ............... | 709/224 |
| 2005/0239192 A1 | 10/2005 | Nasarabadi et al. | | |
| 2006/0003396 A1 | 1/2006 | Spivey et al. | | |
| 2006/0057599 A1 | 3/2006 | Dzenitis et al. | | |

(Continued)

OTHER PUBLICATIONS

Parker, A., "Detecting Bioaerosols When Time Is of the Essence," Lawrence Livermore National Laboratory, 2004 R&D Awards, S&TR Oct. 2004, 2 pages.

(Continued)

*Primary Examiner*—Edward R Cosimano
(74) *Attorney, Agent, or Firm*—Eddie E. Scott; John H. Lee (57) ABSTRACT

A method of detecting real events by obtaining a set of recent signal results, calculating measures of the noise or variation based on the set of recent signal results, calculating an expected baseline value based on the set of recent signal results, determining sample deviation, calculating an allowable deviation by multiplying the sample deviation by a threshold factor, setting an alarm threshold from the baseline value plus or minus the allowable deviation, and determining whether the signal results exceed the alarm threshold.

18 Claims, 6 Drawing Sheets

U.S. PATENT DOCUMENTS

2006/0267756 A1* 11/2006 Kates .......................... 340/521
2006/0273896 A1* 12/2006 Kates ..................... 340/539.18
2007/0139183 A1*  6/2007 Kates .......................... 340/521
2008/0016412 A1*  1/2008 White et al. ................... 714/48
2008/0097637 A1*  4/2008 Nguyen et al. .............. 700/110

OTHER PUBLICATIONS

Parker, A., "Rapid Field Detection of Biological Agents," Livermore National Laboratory, Science & Technology Review, Jan./Feb. 2002, 4 pages.

* cited by examiner

DETECTION AND QUANTIFICATION SYSTEM FOR MONITORING INSTRUMENTS

The United States Government has rights in this invention pursuant to Contract No. W-7405-ENG-48 between the United States Department of Energy and the University of California for the operation of Lawrence Livermore National Laboratory.

BACKGROUND

1. Field of Endeavor

The present invention relates to detection and quantification and more particularly to a detection and quantification system for monitoring instruments.

2. State of Technology

International Patent Application No. WO 2005/001435 by The Regents of the University of California for an autonomous monitoring system for monitoring for bioagents published Jan. 6, 2005 provides the following state of technology information: "Long before the anthrax letter attacks, scientists at two of the U.S. Department of Energy's national laboratories, Lawrence Livermore National Laboratory (LLNL) and Los Alamos National Laboratory (LANL), were busy pioneering a 'biodetector' akin to a smoke detector to rapidly detect the criminal use of biological agents . . . . The Autonomous Pathogen Detection System (APDS) is a file-cabinet-sized machine that sucks in air, runs tests, and reports the results itself. APDS integrates a flow cytometer and real-time PCR detector with sample collection, sample preparation, and fluidics to provide a compact, autonomously operating instrument capable of simultaneously detecting multiple pathogens and/or toxins. The system is designed for fixed locations, says Langlois, where it continuously monitors air samples and automatically reports the presence of specific biological agents. APDS is targeted for domestic applications in which the public is at high risk of exposure to covert releases of bioagents—subway systems, transportation terminals, large of flee complexes, and convention centers APDS provides the ability to measure up to 100 different agents and controls in a single sample," Langlois says.

United States Published Patent Application No. 2006/0057599 by John M. Dzenitis et al for a system for autonomous monitoring of bioagents published Mar. 16, 2006 provides the following state of technology information: "At present there are more than 30 pathogens and toxins on various agency threat lists. Public health personnel rarely see most, of the pathogens so they have difficulty identifying them quickly. In addition, many pathogenic infections aren't immediately symptomatic, with delays as long as several days, limiting options to control the disease and treat the patients. The lack of a practical monitoring network capable of rapidly detecting and identifying multiple pathogens or toxins on current threat lists translates into a major deficiency in the United States ability to counter biological terrorism . . . . The (2006/0057599) invention provides an autonomous monitoring apparatus for monitoring air, water, soil, or other substance for bioagents. A collector gathers a quantity of the air, water, soil, or other substance being monitored. The collector separates selected potential bioagent particles from the air, water, soil, or other substance that is being collected. A sample preparation system prepares a sample of the selected potential bioagent particles. The sample is analyzed by a system for detecting said bioagents."

United States Published Patent Application No. 2003/0148332 by Roger Taylor et al for adaptive baseline algorithm for quantitative PCR published Aug. 7, 2003 provides the following state of technology information: "The (Patent Application No. 2003/0148332) invention relates to algorithms for calculating an adaptive baseline of a PCR reaction, computer program products comprising the same, systems implementing the algorithms and methods for using the same. The algorithm calculates an adaptive baseline for data obtained from one or more labels evaluated in an amplification reaction. In one aspect, the method measures an actual signal obtained during a PCR cycle and generates a first plot for each one or more labels, determines a starting cycle and an ending cycle for one or more labels and calculates an adaptive baseline for each sample or label. The adaptive baseline can be subtracted from the actual signal observed during a PCR amplification cycle and used to calculate the amount of a nucleic acid template in a PCR reaction."

European Patent Application No. EP1576353 by The Regents of the University of California for an autonomous monitoring system for monitoring for bioagents published Aug. 11, 2005 provides the following state of technology information: "There exists a critical need to develop distributed biothreat agent sensor networks that can operate in civilian applications. To operate in 'Detect to Protect/Warn' type detection architectures, these platforms need to have several key properties. They need to be capable of detecting pathogens within a 1-2 hour time window, allowing for enough time to respond to an event. They need to be extremely low cost to maintain, since continuous monitoring is essential for many applications. These platforms need to have sufficient sensitivity to cover a broad geographical area (limiting the necessary number of sensors) and have sufficient selectivity to virtually eliminate false positives."

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

Applications exist that require monitoring infrequent data signals (approximately hourly) and making potentially high-impact decisions based on that data. The difficulty lies in analyzing the data to recognize an increase that represents a real signal against background noise that can fluctuate over time. This must be done in a manner to give low and controllable probability of false positive while maintaining the best possible sensitivity. An earlier "fixed-threshold method" for meeting the applications set a fixed limit for the data signals. To get acceptably low levels of false positives in the face of several sources of noise, the thresholds had to be set rather high. This led to poor system sensitivity. A second "relative ratio method" compared the relative responses of several assay channels in a correlation to avoid noise that caused all signals to change at once. This generally improved the sensitivity, but the minimum achievable probability of false positives was not as low as desired.

The present invention provides a method of detecting real events using a detector that produces signal results at regular intervals. The method distinguishes the real events from noise or variation over time. The method includes the steps of obtaining a set of recent signal results, calculating measures of the noise or variation based on the set of recent signal results, calculating an expected baseline value based on the set of recent signal results, determining sample deviation, calculating an allowable deviation by multiplying the sample deviation by a threshold factor, setting an alarm threshold from the baseline value plus or minus the allowable deviation, and determining whether the signal results exceed the alarm threshold.

The present invention provides a method of detecting real events (signal) from background data (noise) when monitoring biological or other data over time. The system provides a better combination of sensitivity and low false positives than other approaches. The present invention has many uses. In one embodiment, the present invention is employed in an Autonomous Pathogen Detection System (APDS). The present invention has a much wider application to other instruments such as radiation detection. The present invention is particularly useful for data where the signals have significant noise and the data rate is low so high-impact actions are taken based on only one or two samples.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF THE INVENTION

Referring to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

The present invention is described in connection with data analysis and interpretation for the Autonomous Pathogen Detection System (APDS). It is to be understood that the present invention can be used with other systems and is not limited to APDS systems. The APDS is described in International Patent Application No. WO 2005/001435 by The Regents of the University of California for an autonomous monitoring system for monitoring for bioagents published Jan. 6, 2005. International Patent Application No. WO 2005/001435 by The Regents of the University of California for an autonomous monitoring system for monitoring for bioagents published Jan. 6, 2005 is incorporated herein by this reference. The APDS is also described in the article "Rapid Field Detection of Biological Agents" in the January/February 2002 issue and the article "Detecting Bioagents When Time is of the Essence" in the October 2004 issue of Science and Technology Review. The article "Rapid Field Detection of Biological Agents" in the January/February 2002 issue and the article "Detecting Bioagents When Time is of the Essence" in the October 2004 issue of Science and Technology Review are incorporated herein by this reference.

Figure 1:
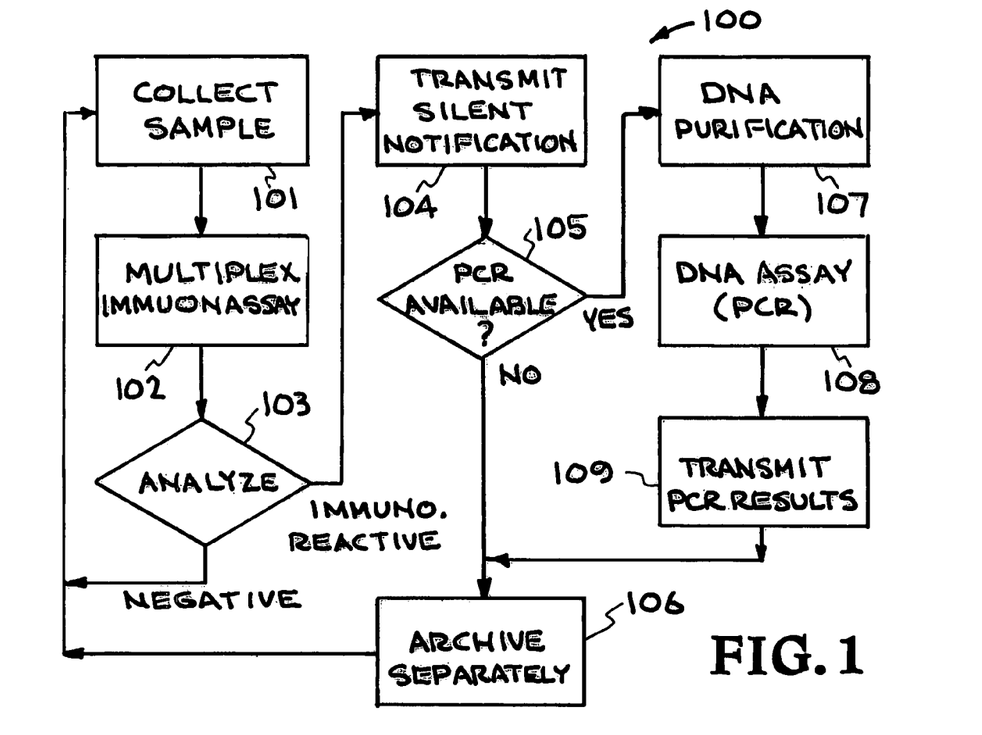
FIG. 1 is a process flow diagram for an APDS unit for environmental monitoring.

Referring now to FIG. 1 a process flow diagram for an APDS unit for environmental monitoring is shown. The APDS system is designated generally by the reference numeral 100. As show in FIG. 1 the system 100 includes boxes collect sample 101, multiplex immunoassay 102, analyze 103, transmit silent notification 104, PCR available 105, archive separately 106, DNA purification 107, DNA assay (PCR) 108 and transmit PCR results 109. Most of the time, the system 100 will operate in the column shown on the left. An immunoassay result for any agent that is above the detection threshold set for that agent is considered "positive" and will result in a notification text message being sent. Confirmatory PCR (indicated in the column on the right) will be performed provided the immunoassay reactive agent contains DNA. In order to operate autonomously, the system must perform automatic analysis of the immunoassay so the system can send an alert and immediately run the confirmatory PCR assay.

The detection algorithm uses standard deviations ($\sigma$, or sigma) multiplied by a factor (N), so is referred to as the "N-sigma method." In one embodiment, the recent historical data in a moving window is analyzed by a form of regression to generate an expected value for the next data point. The historical data is also analyzed to determine a standard deviation from noise, and a multiple of this standard deviation is added to the expected value to determine the threshold. A better sensitivity/false positive performance has been obtained with this general approach than with earlier fixed-threshold and relative-ratio methods. The shapes of the curves indicate that significantly lower probabilities, which may be of interest, will be reached at higher N-sigma. Quantification of signals over the threshold in terms of agent concentration can be performed using a simple equation with two calibration parameters.

Figure 2:
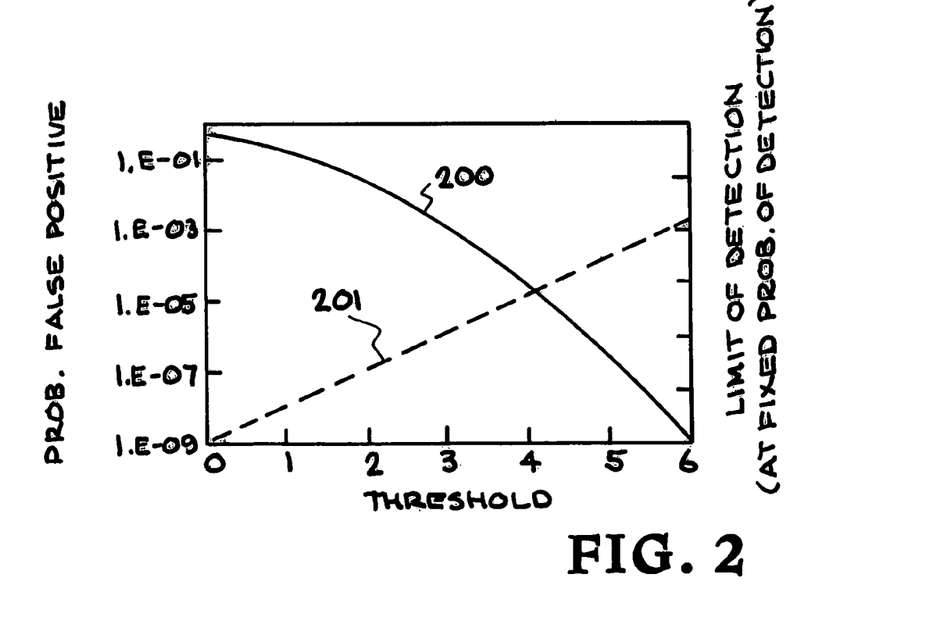
FIG. 2 shows a theoretical example of threshold setting affecting both probability of false immunoassay reactive result and limit of detection.

When considering signals from a pathogen detection instrument, the most important question is whether a given data point is likely to be from real presence of agent or not (probability of false positive). If the signal is real, then the next question is how much agent caused the signal (quantitation). The associated issue is the minimum concentration that the instrument could detect (sensitivity, or limit of detection at a given probability of detection). In most cases there is some adjustable threshold that affects both the probability of false positive and the sensitivity, and these two parameters are inversely related. This is illustrated with theoretical Gaussian behavior in FIG. 2. FIG. 2 shows a theoretical example of threshold setting affecting both probability of false immunoassay reactive result (solid curve 200) and limit of detection (dashed curve 201). This is one form of a Receiver Operating Characteristic (ROC) curve that is useful for choosing threshold settings; the same data can be plotted as probability versus limit of detection to summarize instrument performance.

Detection Algorithm Overview

The N-Sigma Algorithm to determine positive results provides the automated ability to determine if an agent's signal suggests the presence of the agent. The signal is compared to an allowable threshold that is determined by an expected baseline value plus a number of standard deviations, or N-sigma.

The algorithm has two stages that cycle with every new sample update. The first is to estimate the new value of the baseline, and the second is to determine if the new sample is indeed positive.

The present invention provides a method of using detection algorithms for biological detection by (1) amassing a substantial set of results known to be negative, (2) selecting a detection algorithm with adjustable threshold parameters, (3) analyzing the set of negative results with the detection algorithm to determine the fraction of false positives across a range of threshold parameters, (4) selecting the threshold parameters based on desired probability of false positives. In one embodiment of the present invention the detection algorithm involves calculating measures of noise or variation as sample deviation, calculating expected baseline values, calculating an allowable deviation by multiplying the sample deviation by a threshold factor, setting an upper and lower alarm threshold from the baseline value plus or minus the allowable deviation, and determining if the current signal exceeds the alarm thresholds. In one embodiment of the present invention the baseline value is constructed to minimize the estimation error by using a covariance matrix of the noise. In one embodiment of the present invention the sample deviation is the standard deviation of the recent signal results. In one embodiment of the present invention the baseline value is constructed to minimize the estimation error by using a covariance matrix of the noise and the sample deviation is the standard deviation of the recent signal results.

Figure 3:
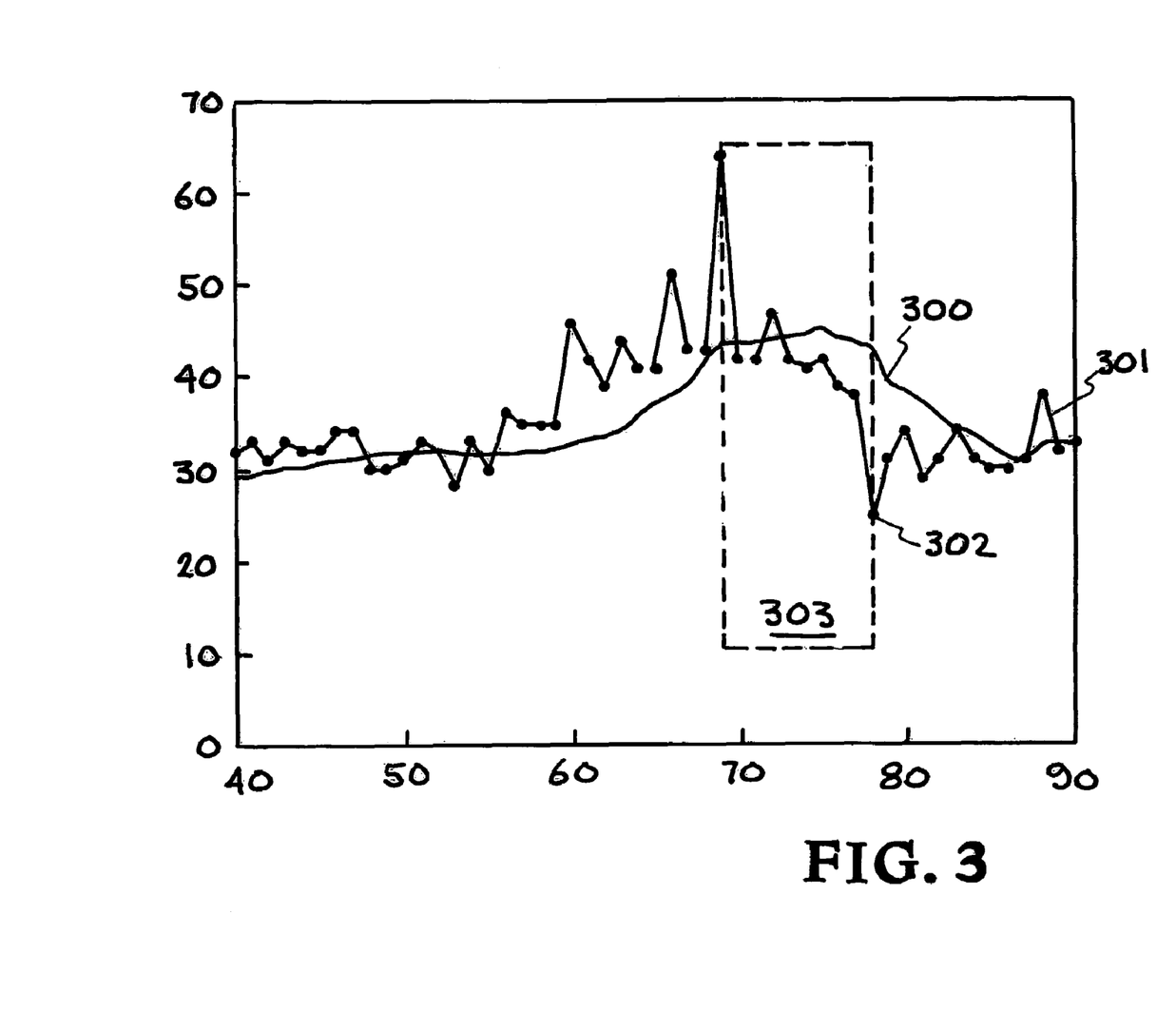
FIG. 3 illustrates an example of trending of biological assay signal (MFI versus sample number) showing a baseline and a processing window.

Referring now to FIG. 3, an example of trending of biological assay signal (MFI versus sample number) is provided showing baseline 300 and a processing window 303. As show in FIG. 3 the system includes boxes Baseline $b_k$ 300, MFI Signal 301, Sample 302, and Processing Window 303. The estimation of the MFI baseline b for sample 302 is based on a fixed number L of previous measurements (typically based on the 10 previous measurements) defined as the processing window 303. We then assume that every measurement within the processing window of sample $z_k$ is an estimation of $b_k$ with some noise. We have the following system of equations within the processing window 303

$$\begin{cases} z_k = b_k + n_{k,0} \\ z_{k-1} = b_k + n_{k,1} \\ \ldots \\ z_{k-L+1} = b_k + n_{k,L-1} \end{cases} \quad 1)$$

which can be written into a matrix form as follows $$\begin{pmatrix} z_k \\ z_{k-1} \\ \ldots \\ z_{k-L+1} \end{pmatrix} = \begin{pmatrix} 1 \\ 1 \\ \ldots \\ 1 \end{pmatrix} b_k + \begin{pmatrix} n_{k,0} \\ n_{k,1} \\ \ldots \\ n_{k,L-1} \end{pmatrix} \text{ or } Z_k = H \cdot b_k + N_k. \quad 2)$$

where the capitalized notation represents a vector.

We must note that a sample $z_{k-i}$ was used to estimate a different baseline point for previous processing windows.

The weighted recursive least square baseline estimate solution minimizes a quadratic cost function of the error introduced by the noise vector $N_k$ and is shown below with $S_k$ as a symmetric weighting matrix:

$$b_k = \underbrace{(H^t \cdot S_k \cdot H)^{-1} \cdot H^t \cdot S_k \cdot Z_k}_{\text{Estimation}} - \underbrace{(H^t \cdot S_k \cdot H)^{-1} \cdot H^t \cdot S_k \cdot N_k}_{\text{Error}} \quad 3)$$

Choosing $S_k$ as the covariance matrix of the noise $N_k$ gives the best unbiased linear estimation of $b_k$ given below.

$$\tilde{b}_k = (H^t \cdot S_k \cdot H)^{-1} \cdot H^t \cdot S_k Z_k \quad 4)$$

To simplify the covariance matrix calculation at each time step, we assume noise is uncorrelated between samples and can have different spread range (defined by the variance) at each measurement. Noise is uncorrelated since each measurement is independent from previous ones as they are performed on different collection samples and the fluidics are cleaned in-between. The noise spread range is validated in recognizing instrument conditions, such as temperature, change for each measurement yielding different uncertainties. The covariance matrix is then:

$$S_k = \begin{pmatrix} 1/\sigma_{k,0}^2 & 0 & \ldots & 0 \\ 0 & 1/\sigma_{k,1}^2 & \ldots & 0 \\ \ldots & \ldots & \ldots & 0 \\ 0 & 0 & \ldots & 1/\sigma_{k,L-1}^2 \end{pmatrix} \quad 5)$$

where the $\sigma_{k,i}$ are the standard deviations of the noise components $n_{k,i}$. This weighting matrix "rewards" the less noisy samples in the processing window. To compute each element, we compute the standard deviation across the set of samples within the processing window associated to sample zk using the standard equation $$\sigma_{k,i}^2 = \frac{1}{L} \sum_{j=0}^{L-1} (z_{k-i-j} - \mu_{k-i})^2 \text{ where } \mu_i = \frac{1}{L} \sum_{j=0}^{L-1} z_{i-j}. \quad 6)$$

Figure 4:
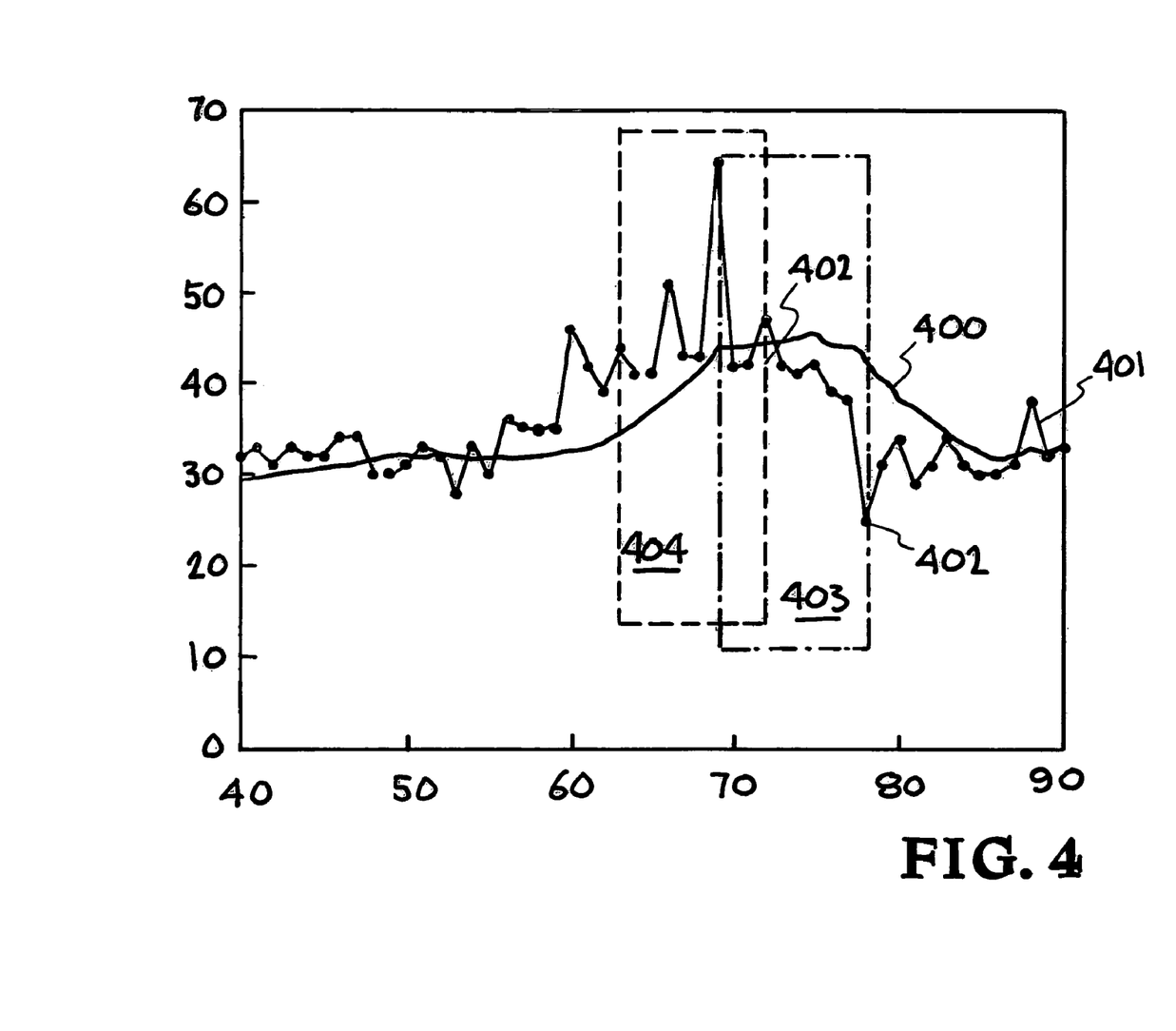
FIG. 4 illustrates an example of trending of biological assay signal showing a window for computing standard deviation for a point in the past.

Referring now to FIG. 4 an example of trending of biological assay signal is provided showing a window for computing standard deviation for a point in the past. As show in FIG. 4 the system includes boxes Baseline $b_k$ 400, MFI Signal 401, Sample 402, Processing Window 403, and Processing Window 404.

In this case, we then have $\sigma_{k,i} = \sigma_{k-i,0} = \sigma_{k-i}$. This reduces the number of computations since only one new sigma value needs to be computed in a new processing window ($\sigma_{k,0}$) and all the other values have already been estimated for the previous processing window.

Because of the form of Equation 2, it is possible to simplify Equation 4. We then have $$\tilde{b}_k = \frac{\sum_{j=0}^{L-1} z_{k-j} \frac{1}{\sigma_{k-j}^2}}{\sum_{j=0}^{L-1} \frac{1}{\sigma_{k-j}^2}}. \qquad 7)$$

Once the baseline is estimated, we have a reference point that defines what is expected for the current point. The next step is to autonomously determine if the most recent MFI sample is significantly different from the expected value and therefore positive. The N-Sigma method used in this algorithm consists of computing the MFI variance to the estimated baseline over the processing window. The sigma (standard deviation) is obtained as the square root of the variance. We can then define a threshold value by adding N values of sigma to the estimated baseline. If the current MFI sample is above that threshold, we then declare an immunoassay positive result. N can be any real positive number. The traditional 3-sigma method would set N for limit of detection (LOD) to 3.0, but in practice the statistical distribution of the data and tolerance to false positives will determine the appropriate N.

Figure 5:
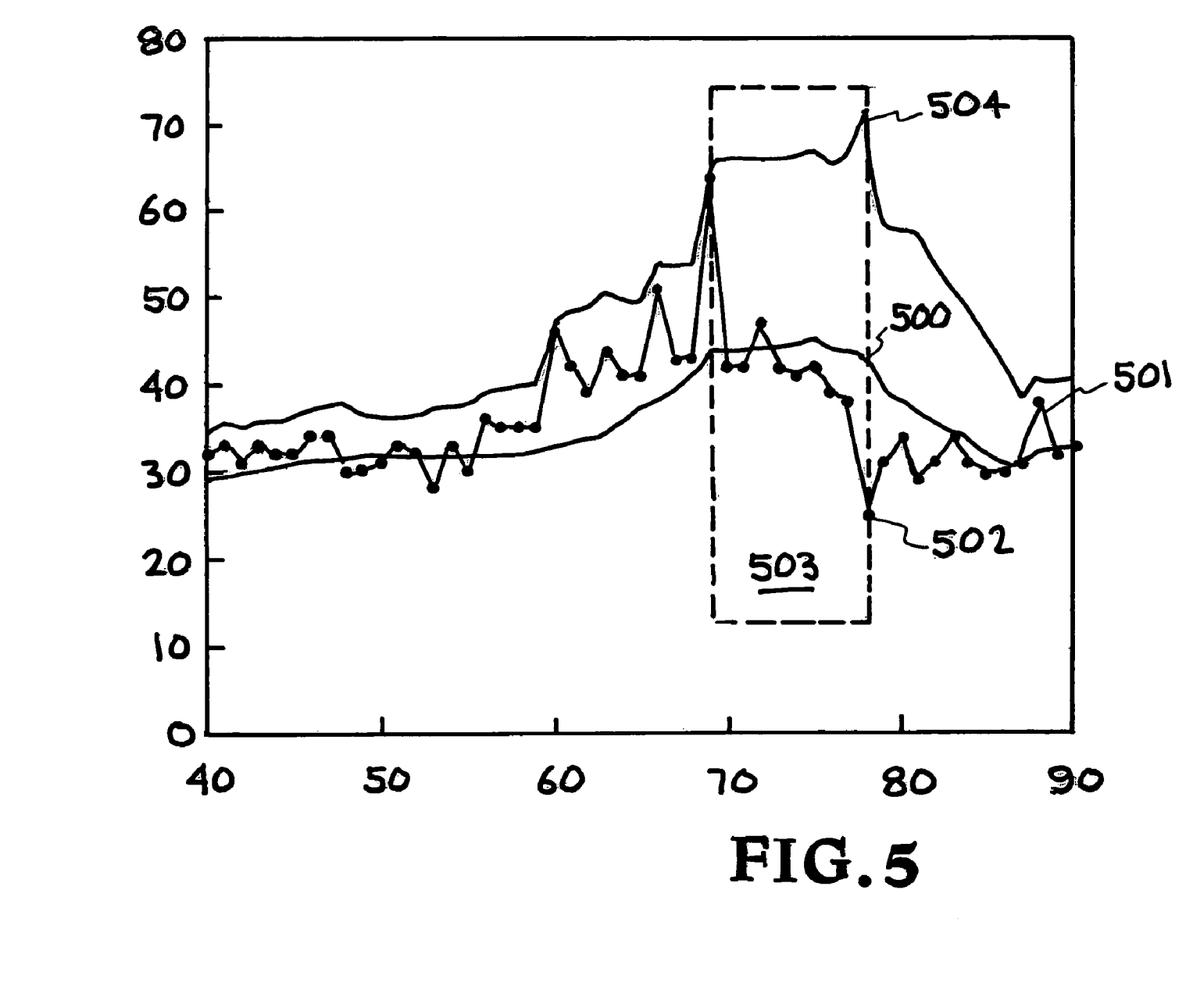
FIG. 5 illustrates another example of trending of biological assay signal with a window for computing standard deviation for a point in the past.

Referring now to FIG. 5 an example of trending of biological assay signal with a window for computing standard deviation for a point in the past is shown. As show in FIG. 5 the system includes boxes Baseline $b_k$ 500, MFI Signal 501, Sample 502, Processing Window 503, and Threshold 504.

The N-Sigma method has a number of advantages including: (1) The method is based on the most common analytical chemistry LOD approach and can reduce to that approach exactly for steady data, (2) The method automatically "learns" and adapts for different instrument and environment noise conditions, and (3) The internal control signals can be processed using the same method, allowing automatic detection of invalid measurements once they cross a given N-sigma threshold.

Variation "without current point": The baseline and threshold estimation as defined in the original algorithm makes use of the current point to estimate what the values should be for that current time step. However, if a positive result is present, this current point should be "abnormal" and therefore artificially affect the estimations. The idea of the variation, then, is to use a window of points in the baseline estimation containing only points before the current time step. However, this variation of the baseline estimation algorithm requires then a higher N-Sigma value in the detection algorithm, as it lowers the overall sigma within the window where typically all the values are similar. This in itself is acceptable, but further study showed that for this data set, at least, the performance of this variation was worse than the standard version including the current point. We used current point version in the rest of the analysis.

Variation "minimum sigma": The basic N-Sigma algorithm simply multiplies the sigma values over the considered window of interest by a set value N and adds it to the baseline estimation in order to define a threshold. One variation is to include a "minimum sigma" value that is a constant. This is included to address the fact that, in unusually stable cases, background data can have very small variations from one time step to another and can even have several time steps with the same MFI values due to rounding in the detector results. This combination will yield a value for sigma that is close to or equal to zero. Such sigma values will provide threshold values artificially close to or equal to the baseline, making any small subsequent variation appear positive. The idea in this variation is to bind the value of sigma to a minimum reasonable value. This prevents stable background data set from giving a false positive on noise when the sigma is close or equal to zero. The effect of minimum sigma is explored below.

For the various algorithms, several parameters can then be optimized. The following optimizations have been investigated.

Window length: The window length defines the number of previous points used to estimate the baseline and the sigma value of the noise. The longer the window, the more accurate the estimation is for a fixed set of data. However, a longer window means a longer period of time before the algorithm can be effective, and it makes the estimate response more sluggish if there are short-term variations. A value of 10 was chosen as a good trade-off between performance and time.

N-sigma value for the controls: An algorithm similar to that used on the agents is used on the controls to determine if the system is stable. When a control triggers, the results across the board are rejected as invalid. We can therefore optimize the value of the N in order to get the optimum trade-off between maximizing number of valid points considered and minimizing overall probability of false positive. A value of 3.0 for the basic original algorithm provided a good trade-off.

Minimum Sigma value (when applicable): When the version of the algorithm including a minimum sigma is used, it is possible to optimize that value. A minimum sigma limit too low will increase the overall probability of false positive when background is constant. A minimum sigma limit too high will reduce the sensitivity of the instrument by increasing the limit of detection in terms of concentration detected. We must note that the trade-off also considers performance at different concentration of agents for the sensitivity.

The minimum sigma should be set to a value that improves the probability of false positive relative to not using a minimum sigma (equivalent to a zero minimum sigma value) for all the concentration tested. We should not allow the minimum sigma to improve some concentration and worsen others. In FIG. 5, for example, we are looking for improvements relative to a small minimum sigma of 0.1. We would choose 1.2 as it improves all three lower LOD concentrations (LOD1 to LOD3). For this particular data set, the higher concentrations (LOD4 to LOD7) do not have false positives with or without using a minimum sigma.

N-sigma value for the agents: This is the main parameter defining how the instrument will perform. The optimization of this parameter is based on the trade-off between probability of false positive result and limit of detection. The probability curve is based on background field data from relevant environments. The limit of detection curve is based on spiking data with known concentrations, a selected probability of detection, and in some cases background noise.

All of the parameters described in this section could be optimized at once. In practice, the parameters except N-sigma values for the agents are optimized together to make a given algorithm perform at its best across most reasonable conditions. The N-sigma values for each agent assay remain as the adjustable parameter to be determined with the end-users, primarily determined by their tolerance to false immunoassay positive results. Once that parameter is set, the probability of a false immunoassay positive is set.

DESCRIPTION OF PREFERRED EMBODIMENT

The present invention provides a method of detecting real events from noise over time in a detector that provides signal results at regular intervals by (1) calculating measures of noise or variation (sample deviations, a) based on a set of recent signal results, (2) calculating expected baseline values (sample baseline, b) based on a set of recent signal results, (3) calculating an allowable deviation by multiplying the sample deviation by a threshold factor, N, (4) setting an upper and lower alarm threshold from the baseline value plus or minus the allowable deviation ($T_h^+ = b + N\sigma$ and $T_h^- = b - N\sigma$), and (5) determining if the current signal $z_k$ exceeds the alarm thresholds, $z_k > T_h^+$ or $z_k < T_h^-$. The method is adaptive because the sample baseline and the sample deviation can vary over time depending on the detector performance. The detector can be a biological detector, a radiation detector or other detector. In one embodiment the baseline value is the arithmetic mean of the set of recent signal results. In one embodiment the baseline value is constructed to minimize the estimation error by using a covariance matrix of the noise, effectively weighting the recent signal results by their variances. In one embodiment the recent signal results include the current data point in consideration. In one embodiment the recent signal results omit the current data point in consideration. In one embodiment the sample deviation is the standard deviation of the recent signal results. In one embodiment the sample deviation is the standard deviation of the recent signal results and the recent signal results include the current data point in consideration. In one embodiment the sample deviation is the standard deviation of the recent signal results and the recent signal results omit the current data point in consideration. In one embodiment the baseline value is constructed to minimize the estimation error by using a covariance matrix of the noise, effectively weighting the recent signal results by their variances, and the sample deviation is the standard deviation of the recent signal results. In one embodiment the baseline value is constructed to minimize the estimation error by using a covariance matrix of the noise, effectively weighting the recent signal results by their variances, and the sample deviation is the standard deviation of the recent signal results and the recent signal results include the current data point in consideration. In one embodiment the baseline value is constructed to minimize the estimation error by using a covariance matrix of the noise, effectively weighting the recent signal results by their variances, and the sample deviation is the standard deviation of the recent signal results and the recent signal results omit the current data point in consideration.

Figure 6:
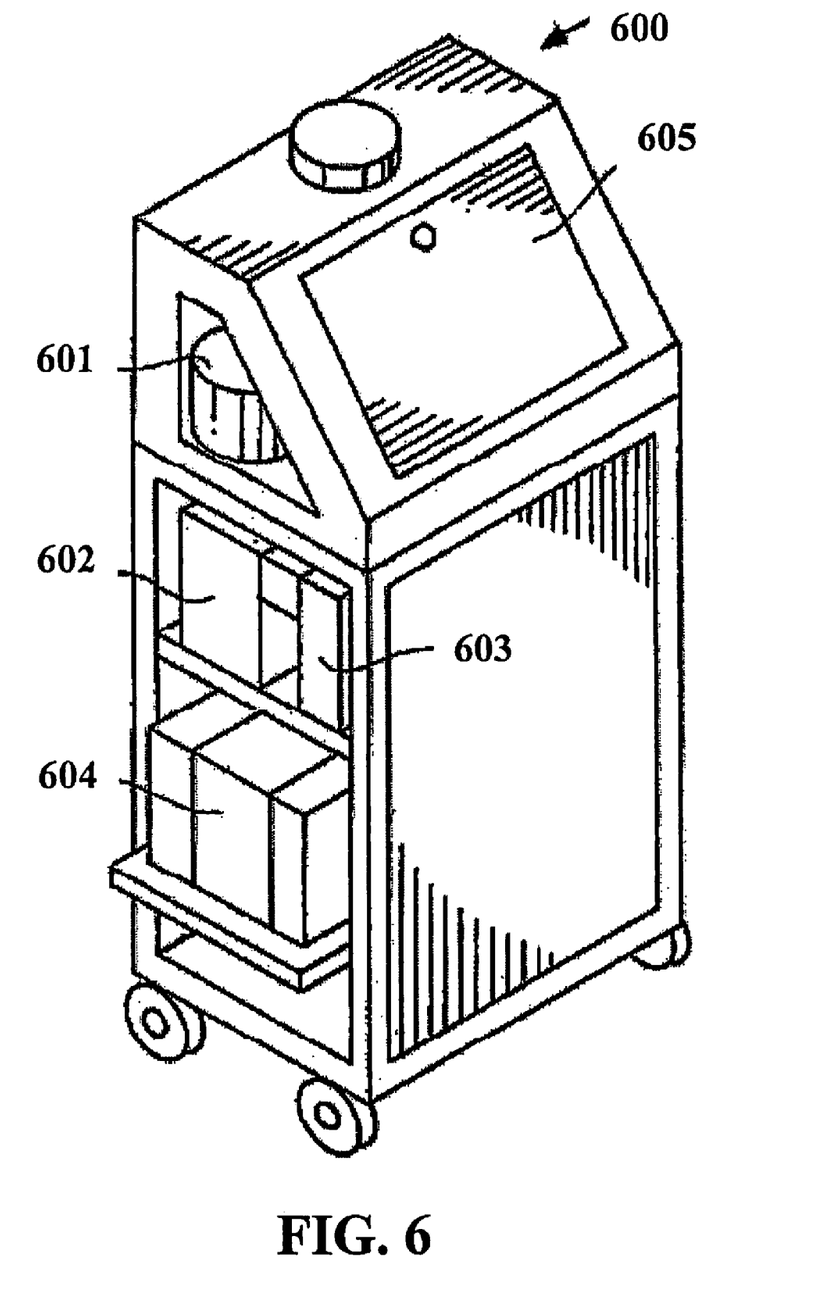
FIG. 6 shows an autonomous pathogen detection system (APDS) device.

Referring now to FIG. 6, one embodiment of an Autonomous Pathogen Detection System (APDS) is shown. The APDS system is designated generally by the reference numeral 600. The APDS is described in International Patent Application No. WO 2005/001435 by The Regents of the University of California for an autonomous monitoring system for monitoring for bioagents published Jan. 6, 2005. International Patent Application No. WO 2005/001435 by The Regents of the University of California for an autonomous monitoring system for monitoring for bioagents published Jan. 6, 2005 is incorporated herein by this reference. The APDS is also described in the article "Rapid Field Detection of Biological Agents" in the January/February 2002 issue and the article "Detecting Bioagents When Time is of the Essence" in the October 2004 issue of Science and Technology Review. The article "Rapid Field Detection of Biological Agents" in the January/February 2002 issue and the article "Detecting Bioagents When Time is of the Essence" in the October 2004 issue of Science and Technology Review are incorporated herein by this reference.

An air sample is collected by the air collection system 601. The next step is detection of any pathogens in particles in the air sample. This is accomplished by a liquid-array based multiplex immunoassay detection system 602 and an in-line nucleic acid amplification and detection system 603 shown in FIG. 6. The liquid-array based immunoassay detection system 602 measures multiple pathogen targets in the sample. The immunoassay system 602 can use either "wash assay" system or "no-wash assay" system. The "wash assay" system and the "no-wash assay" system use optically-encoded beads. The beads are kept in a small (~15 mL) stirred tank. Bead loss from agglomeration is reduced by using dispersing agents such as ethanol in the bead slurry. This reduces reagent cost.

The assay system uses a number of reagents in addition to the liquid sample. The reagents include detector antibody, and fluorescent reporter (streptavidin-phycoerythrin). In the wash assay system, a bed of beads is deposited on a filter then exposed to the sample, washing buffer, detector antibody, washing buffer, fluorescent reporter, washing buffer, and then the beads are released to the detector. For the wash assay system, the bead filter performance in releasing beads is improved by implementing frequent clean-in-place protocols using reagents such as bleach for cleaning and morpholine propane sulfonic acid (MOPS) citrate buffer for reconditioning the filter. This extends the time between servicing the instrument and thus reduces operating cost.

The PCR (nucleic acid) amplification and detection system 603 confirms the presence of any bioagent. An archived sample is mixed with the TaqMan reagent, and then introduced by a system into a flow through polymerase chain reaction (PCR) system. Specific nucleic acid signatures associated with the targeted bioagent are amplified and detected using fluorescence generated from nucleic acid replication from the TaqMan probes.

The PCR assays for confirming immunoassay positives are implemented using real-time PCR and the TaqMan process. Both FAM and TAMRA dyes are used as TaqMan reporters and TAMRA and BHQ (Black Hole Quencher) dyes are used as TaqMan quenchers. In one embodiment the FAM-BHQ is used for the bioagent probe and TAMRA-BHQ for an internal control probe. This allows an internal control to be used on a two-color detector. Internal controls are critical in PCR due to the delicacy of the reaction; otherwise, negative results are not definitive. In one embodiment, two-color excitation is used to give strong signals for duplexed TaqMan PCR (agent plus internal control).

Sample preparation moves the sample from the sample collection 601 to appropriate modules within the system. An access panel 605 allows access to the sample collection 601. The nucleic acid assay system 603 includes a number of components including system for injecting/aspirating a sample, system for adding PCR reagent, system for mixing sample and reagent, system for transport to PCR reactor, system for performing PCR amplification, system for transport of amplified sample from PCR reactor for detection of PCR amplicons. A central computer 604 uses a simple serial based LabVIEW control system to control all instrument functions. A software system provides data acquisition, real-time data analysis, and result reporting via a graphical user interface.

The system includes both real-time and post-PCR detection. The system is ideal for monitoring type systems, such as those currently being developed to detect terrorist releases of aerosolized bioagents. On-site detection systems for infectious diseases under development will need to incorporate sample preparation and analysis functions. The system allows relatively unskilled personnel, such as early responders, to perform real-time field or point-of-care nucleic acid assays. In various other embodiments of the autonomous pathogen detection system, the confirmation of bioagent(s) in the sample is provided by a multiplex immunoassay detector, a multiplex PCR detector, and a real-time PCR detector.

The primary focus of the autonomous pathogen detection system 600 is the protection of civilians from terrorist attacks; however, the system also has a role in protecting military personnel from biological warfare attacks. The autonomous pathogen detection system 600 also has uses in medical facilities and research and development facilities. The autonomous pathogen detection system 600 has uses in medical monitoring. There are a variety of medical applications where monitoring for biological pathogens would be useful. A good example of this is monitoring in hospitals and clinics for highly infectious agents such as tuberculosis or nosocomial diseases that can threaten the well being of patients and health care professionals. The autonomous pathogen detection system 100 also has uses in environmental monitoring, that is, any application that would benefit from environmental monitoring of biological species. One example is continuous aerosol monitoring of bacterial and other pathogens that could affect the health of livestock (such as the recent hoof and mouth disease outbreak). Another example is continuous aerosol monitoring of viruses that could affect the health of large portions of the population (such as the recent SARS outbreak).

Figure 7:
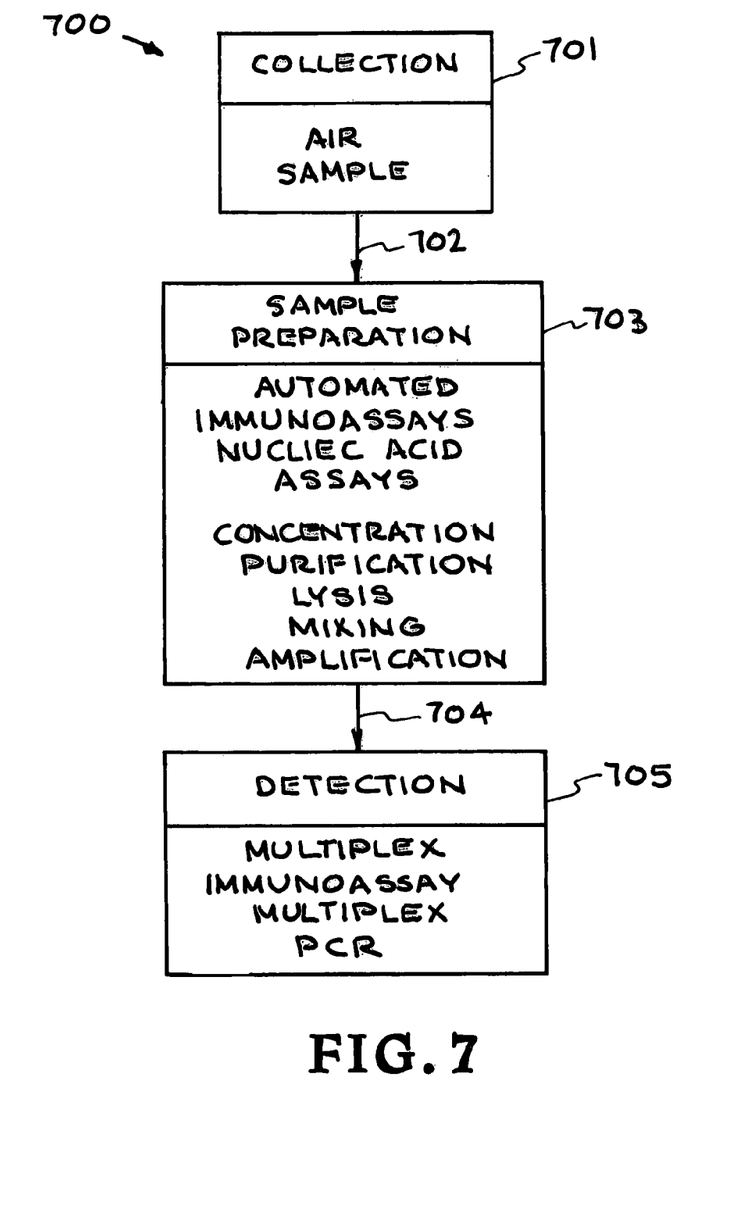
FIG. 7 illustrates a method of the present invention used in an autonomous pathogen detection system (APDS).

Referring now to FIG. 7, the method 700 used in the autonomous pathogen detection system provides collection 701, sample preparation 703, and detection 705. As illustrated in FIG. 7, after collection 701, the sample is transferred as shown by arrow 702 for sample preparation 703. The sample preparation 703 provides an automated sample, an immunoassay sample, and/or a nucleic acid assay sample. In sample preparation 703 the sample may be concentrated, purified, lysed, pulverized or otherwise made to have smaller particulates, mixed, and/or amplified. After sample preparation 703, the sample is transferred as shown by arrow 704 for detection.

The next step is detection of any pathogens in the sample particles. This is accomplished by a liquid-array based multiplex immunoassay detection system 602 and an in-line nucleic acid amplification and detection system 603 shown in FIG. 6. The liquid-array based immunoassay detection system 602 measures multiple pathogen targets in the sample. The immunoassay system 602 can use either "wash assay" system or "no-wash assay" system. The "wash assay" system and the "no-wash assay" system use optically-encoded beads. The beads are kept in a small (~15 mL) stirred tank. Bead loss from agglomeration is reduced by using dispersing agents such as ethanol in the bead slurry. This reduces reagent cost.

The wash assay system uses a number of reagents in addition to the liquid sample. The reagents include detector antibody, and fluorescent reporter (streptavidin-phycoerythrin). In the wash assay system, a bed of beads is deposited on a filter then exposed to the sample, washing buffer, detector antibody, washing buffer, fluorescent reporter, washing buffer, and then the beads are released to the detector. For the wash assay system, the bead filter performance in releasing beads is improved by implementing frequent clean-in-place protocols using reagents such as bleach for cleaning and morpholine propane sulfonic acid (MOPS) citrate buffer for reconditioning the filter. This extends the time between servicing the instrument and thus reduces operating cost.

The PCR (nucleic acid) amplification and detection system 203 confirms the presence of any bioagent. An archived sample is mixed with the TaqMan reagent, and then introduced by a system into a flow through polymerase chain reaction (PCR) system. Specific nucleic acid signatures associated with the targeted bioagent are amplified and detected using fluorescence generated from nucleic acid replication from the TaqMan probes.

The PCR assays for confirming immunoassay positives are implemented using real-time PCR and the TaqMan process. Both FAM and TAMRA dyes are used as TaqMan reporters and TAMRA and BHQ (Black Hole Quencher) dyes are used as TaqMan quenchers. In one embodiment the FAM-BHQ is used for the bioagent probe and TAMRA-BHQ for an internal control probe. This allows an internal control to be used on a two-color detector. Internal controls are critical in PCR due to the delicacy of the reaction; otherwise, negative results are not definitive. In one embodiment, two color excitation is used to give strong signals for duplexed TaqMan PCR (agent plus internal control).

Sample preparation moves the sample from the sample collection to appropriate modules within the system. The nucleic acid assay system includes a number of components including system for injecting/aspirating a sample, system for adding PCR reagent, system for mixing sample and reagent, system for transport to PCR reactor, system for performing PCR amplification, system for transport of amplified sample from PCR reactor for detection of PCR amplicons. A central computer uses a simple serial based LabVIEW control system to control all instrument functions. A software system provides data acquisition, real-time data analysis, and result reporting via a graphical user interface.

The system includes both real-time and post-PCR detection. The system is ideal for monitoring type systems, such as those currently being developed to detect terrorist releases of aerosolized bioagents. On-site detection systems for infectious diseases under development will need to incorporate sample preparation and analysis functions. The system allows relatively unskilled personnel, such as early responders, to perform real-time field or point-of-care nucleic acid assays. In various other embodiments of the autonomous pathogen detection system, the confirmation of bioagent(s) in the sample is provided by a multiplex immunoassay detector, a multiplex PCR detector, and a real-time PCR detector.

The primary focus of the autonomous pathogen detection system 700 is the protection of civilians from terrorist attacks; however, the system also has a role in protecting military personnel from biological warfare attacks. The autonomous pathogen detection system 700 also has uses in medical facilities and research and development facilities. The autonomous pathogen detection system 700 has uses in medical monitoring. There are a variety of medical applications where monitoring for biological pathogens would be useful. A good example of this is monitoring in hospitals and clinics for highly infectious agents such as tuberculosis or nosocomial diseases that can threaten the well being of patients and health care professionals. The autonomous pathogen detection system 700 also has uses in environmental monitoring; that is, any application that would benefit from environmental monitoring of biological species. One example is continuous aerosol monitoring of bacterial and other pathogens that could affect the health of livestock (such as the recent hoof and mouth disease outbreak). Another example is continuous aerosol monitoring of viruses that could affect the health of large portions of the population (such as the recent SARS outbreak).

The method 700 has been implemented on APDS instruments and also in a stand-alone software system called the "APDS Algorithm Viewer." The method 700 is used for post-processing large amounts of data to view results, optimize parameters, and generate outputs like Receiver Operating Characteristic (ROC) curves, probability of false positive versus threshold, and probability of detection versus concentration. The N-Sigma method has several advantages:

- The method is based on the most common analytical chemistry LOD approach and can reduce to that approach exactly for steady data.
- The method automatically "learns" and adapts for different instrument and environment noise conditions.
- The internal control signals can be processed using the same method, allowing automatic detection of invalid measurements once they cross a given N-sigma threshold.
- Better sensitivity/false positive performance has been obtained with this general approach than with earlier fixed-threshold and relative-ratio methods.

Since it involves standard deviations ($\sigma$, or sigma) multiplied by a factor (N), Applicants refer to the algorithm as the "N-sigma method." In its current embodiment, the recent historical data in a moving window is analyzed by a form of regression to generate an expected value for the next data point. The historical data is also analyzed to determine a standard deviation from noise, and a multiple of this standard deviation is added to the expected value to determine the threshold. This allows the thresholds to tighten when there is a low level of noise, giving the best possible sensitivity, and then expand when the signals become noisy, maintaining a low probability of false positive.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A method of detecting real events using a detector that produces signal results at regular intervals, the method distinguishing the real events from noise or variation over time, comprising the steps of:
   obtaining a set of recent signal results representing the real events,
   calculating measures of the noise or variation based on said set of recent signal results,
   calculating an expected baseline value based on said set of recent signal results,
   determining sample deviation of said recent signal results,
   calculating an allowable deviation by multiplying said sample deviation by a threshold factor,
   setting an alarm threshold from said baseline value plus or minus said allowable deviation, and
   determining whether the signal results exceed said alarm threshold.

2. The method of detecting real events of claim 1 wherein said step of calculating an expected baseline value comprises calculating said baseline value as the arithmetic mean of said set of recent signal results.

3. The method of detecting real events of claim 1 wherein said step of calculating an expected baseline value includes minimize estimation error by using a covariance matrix of the noise, effectively weighting the recent signal results by their variances.

4. The method of detecting real events of claim 1 wherein said step of obtaining a set of recent signal results comprises including a current data point.

5. The method of detecting real events of claim 1 wherein said step of obtaining a set of recent signal results comprises omitting a current data point.

6. The method of detecting real events of claim 1 wherein said step of determining sample deviation includes the current data point in consideration.

7. The method of detecting real events of claim 1 wherein said step of determining sample deviation omits the current data point in consideration.

8. The method of detecting real events of claim 1 wherein said step of calculating an expected baseline value comprises minimizing estimation error by using a covariance matrix of the noise, effectively weighting the recent signal results by their variances, and the sample deviation is the standard deviation of the recent signal results.

9. The method of detecting real events of claim 1 wherein said step of setting an alarm threshold comprises setting an upper and a lower alarm threshold from said baseline value plus or minus said allowable deviation.

10. A computer-implemented method of detecting real events using a detector that produces signal results at regular intervals, the method distinguishing the real events from noise or variation over time, comprising the steps of:
   (a) obtaining a set of recent signal results representing the real events,
   (b) calculating measures of the noise or variation based on said set of recent signal results,
   (c) calculating an expected baseline value based on said set of recent signal results,
   (d) determining sample deviation of said recent signal results
   (e) calculating an allowable deviation by multiplying said sample deviation by a threshold factor,
   (f) setting an alarm threshold from said baseline value plus or minus said allowable deviation, and
   (g) determining whether the signal results exceed said alarm threshold.

11. The method of detecting real events of claim 10 wherein said step of calculating an expected baseline value comprises calculating said baseline value as the arithmetic mean of said set of recent signal results.

12. The method of detecting real events of claim 10 wherein said step of calculating an expected baseline value includes minimize estimation error by using a covariance matrix of the noise, effectively weighting the recent signal results by their variances.

13. The method of detecting real events of claim 10 wherein said step of obtaining a set of recent signal results comprises including a current data point.

14. The method of detecting real events of claim 10 wherein said step of obtaining a set of recent signal results comprises omitting a current data point.

15. The method of detecting real events of claim 10 wherein said step of determining sample deviation includes the current data point in consideration.

16. The method of detecting real events of claim 10 wherein said step of determining sample deviation omits the current data point in consideration.

17. The method of detecting real events of claim 10 wherein said step of calculating an expected baseline value comprises minimizing estimation error by using a covariance matrix of the noise, effectively weighting the recent signal results by their variances, and the sample deviation is the standard deviation of the recent signal results.

18. The method of detecting real events of claim 10 wherein said step of setting an alarm threshold comprises setting an upper and a lower alarm threshold from said baseline value plus or minus said allowable deviation.

* * * * *